US006280383B1

(12) United States Patent
Damadian (10) Patent No.: US 6,280,383 B1
(45) Date of Patent: Aug. 28, 2001

(54) MAGNETIC RESONANCE IMAGING

(75) Inventor: Raymond V Damadian, Woodbury, NY (US)

(73) Assignee: Fonar Corporation, Melville, NY (US)

(*) Notice: Subject to any disclaimer, the term of this patent is extended or adjusted under 35 U.S.C. 154(b) by 0 days.

(21) Appl. No.: 09/320,998

(22) Filed: May 27, 1999

Related U.S. Application Data (63) Continuation-in-part of application No. 08/948,218, filed on Oct. 9, 1997, now abandoned, which is a continuation of application No. 08/457,868, filed on Jun. 1, 1995, now abandoned, which is a division of application No. 08/024,324, filed on Mar. 1, 1993, now Pat. No. 5,647,361.

(51) Int. Cl.$^7$ .................................................. A61B 5/055
(52) U.S. Cl. ............................................................ 600/410
(58) Field of Search ..................................... 600/309, 363, 600/410, 419, 420; 604/500, 508, 514

(56) References Cited

U.S. PATENT DOCUMENTS

| | | |
|---|---|---|
| 4,431,968 | 2/1984 | Edelstein et al. . |
| 4,586,511 | 5/1986 | Clark, Jr. . |
| 4,775,522 | 10/1988 | Clark, Jr. . |
| 4,984,574 | 1/1991 | Goldberg et al. . |
| 4,993,415 | 2/1991 | Long . |
| 4,996,041 * | 2/1991 | Arai et al. ............................. 600/420 |
| 5,234,680 | 8/1993 | Rogers, Jr. et al. . |
| 5,339,814 * | 8/1994 | Lasker ................................. 600/420 |
| 5,433,196 | 7/1995 | Fiat . |
| 5,479,924 | 1/1996 | Navon et al. . |
| 5,545,396 | 8/1996 | Albert et al. .......................... 424/9.3 |

OTHER PUBLICATIONS

Jain, K.K., *Textbook of Hyperbaric Medicine*, Hogrefe & Hubie (1990), pp. 193–202.

"Hyperbaric Oxygen Therapy of Diabetes–Related Foot Injuries", American Diabetes Association (Undated).

*Clinical Magnetic Resonance Imaging*, vol. 1, edited by R. Edelman et al., "Stroke and Cerebral Ischemia", by T.M. Simonson et al., pp. 767–786, 2d ed. (1991).

J.H. Duijn et al., "Human Brain Infarction: Proton MR Spectroscopy", Radiology 1992; 183:711–718.

D. Sappey–Marinier et al., "Decreased Phosphorus Metabolite Concentrations and Alkalosis in Chronic Cerebral Infarction", Radiology 1992; 182:29–34.

L.L. Baker et al., "Recent Advances in MR Imaging/Spectroscopy of Cerebral Ischemia", AJR 156:1133–1143, Jun. 1991.

R. Tuner et al., "Functional Mapping of the Human Visual Cortex at 4 and 1.5 Tesla Using Deoxygenation Contrast EPI", MRM 29:277–279 (1993).

P.A. Bandettini, "Time Course EPI of Human Brain Function during Task Activation", Magnetic Resonance in Medicine, 25, 390–397 (1992).

K. Kwong et al., "Dynamic magnetic resonance imaging of human brain activity during primary sensory stimulation", Proc. Nat'l. Acad. Sci. USA, vol. 89, pp. 5675–5679, Jun. 1992 Neurobiology.

"Scannig for Tumors", Men's Health, Nov. 1998, p. 42.

\* cited by examiner

*Primary Examiner*—Ruth S. Smith
(74) *Attorney, Agent, or Firm*—Morgan & Finnegan, L.L.P.

(57) ABSTRACT

The present invention is a method of studying tissue metabolism with ordinary oxygen. First, a magnetic resonance image of the tissue of interest is acquired. Oxygen, predominantly in the form of oxygen-16, is then delivered to the tissue. A magnetic resonance image of the tissue of interest is then acquired when the tissue is in the state of increased oxygenation. The first and second images are compared to determine the effect of the delivery of oxygen on the tissue based on changes in image characteristics, such as image contrast, image intensity and the morphology of tissues in the image. A relative measure of the degree of tissue oxygenation before and after the delivery of oxygen may be determined. The oxygen may be administered by inhalation of gaseous oxygen. The tissue may also be directly perfused by gaseous oxygen. The oxygen may be administered in combination with an oxygen carrier molecule, such as hemoglobin or heme. Preferably, only trace amounts of oxygen-17 is present. Oxygen substantially in its naturally occurring isotopic preparations is preferably delivered.

17 Claims, 5 Drawing Sheets

MAGNETIC RESONANCE IMAGING

CROSS-REFERENCE TO RELATED APPLICATIONS

The present application is a continuation-in-part of application, U.S. Ser. No. 08/948,218, filed on Oct. 9, 1997, abandoned which is incorporated by reference herein and is a continuation of U.S. Ser. No. 08/457,868, filed on Jun. 1, 1995, abandoned, which is a division of U.S. Ser. No. 08/024,324, filed on Mar. 1, 1993, which issued as U.S. Pat. No. 5,647,361.

BACKGROUND OF THE INVENTION

The present invention relates to improvements in the use of magnetic resonance imaging, and more particularly to the study of tissue metabolism through the use of oxygen-16.

The ability to produce excellent images of the internal anatomical structure of living beings using nuclear magnetic resonance signals has been well established. Magnetic resonance imaging ("MRI") is highly sensitive to the relaxation times of the nuclei emitting a magnetic resonance signal, and different relaxation times are manifested as different contrasts within the image. The tissues within the various organs and structures of a patient exhibit markedly different relaxation times. Diseased and injured tissue can result in changes in relaxation time relative to healthy tissue. Consequently, MRI produces very high contrast images of anatomical structure, in which injured and diseased tissues are clearly delineated from normal tissue.

Only nuclei containing an odd number of nucleons (protons and neutrons) emit a magnetic resonance signal. While the imaging of oxygen could be useful in the study of tissue metabolism, oxygen-16, the most common isotype of oxygen, has an even number of nucleons and cannot be imaged directly by magnetic resonance imaging. Oxygen-15, which contains an odd number of nucleons, is radioactive and potentially dangerous to the patient. Oxygen-17, which also contains an odd number of nucleons, is not radioactive, but is present in only trace amounts. Enriched oxygen-17 has limited availability and is expensive to prepare. U.S. Pat. No. 5,339,814 to Lasker discloses a process for visualizing tissue metabolism using a gas of an effective imaging amount of oxygen-17. U.S. Pat. No. 4,996,041 to Arai et al. discloses a diagnostic imaging agent including a complex of oxygen-17, a biologically acceptable liquid carrier, such as a perfluorinated compound, and an emulsifying agent. These references do not overcome the disadvantages of the use of oxygen-17.

SUMMARY OF THE INVENTION

The present invention is a method of studying tissue metabolism with oxygen-16. First, a magnetic resonance image of the tissue of interest is acquired. Oxygen, predominantly in the form of oxygen-16, is then delivered to the tissue of interest. A magnetic resonance image of the tissue of interest is then acquired when the tissue is in the state of increased oxygenation. The first and second images are compared to determine the effect of the delivery of oxygen on the tissue. Such effects may manifest themselves as changes in image characteristics, such as image contrast, image intensity and the morphology of the tissue in the images. A relative measure of the degree of tissue oxygenation before and after the delivery of oxygen may also be determined based on the changes in the image characteristics. The changes in image characteristics may also be correlated with the amount of oxygen delivered.

Preferably, only trace amounts of oxygen-17 is present in the oxygen delivered. Oxygen substantially in its naturally occurring isotopic proportions is preferably delivered. The oxygen may be administered by inhalation of gaseous oxygen. The tissue may also be directly perfused by gaseous oxygen. The oxygen may also be administered in combination with an oxygen carrier molecule, such as hemoglobin or heme.

BRIEF DESCRIPTION OF THE DRAWINGS

The objects, features and advantages of the present invention are readily apparent from the detailed description of the preferred embodiments set forth below, in conjunction with the accompanying drawings in which.

DETAILED DESCRIPTION OF THE PREFERRED EMBODIMENTS

Figure 1:
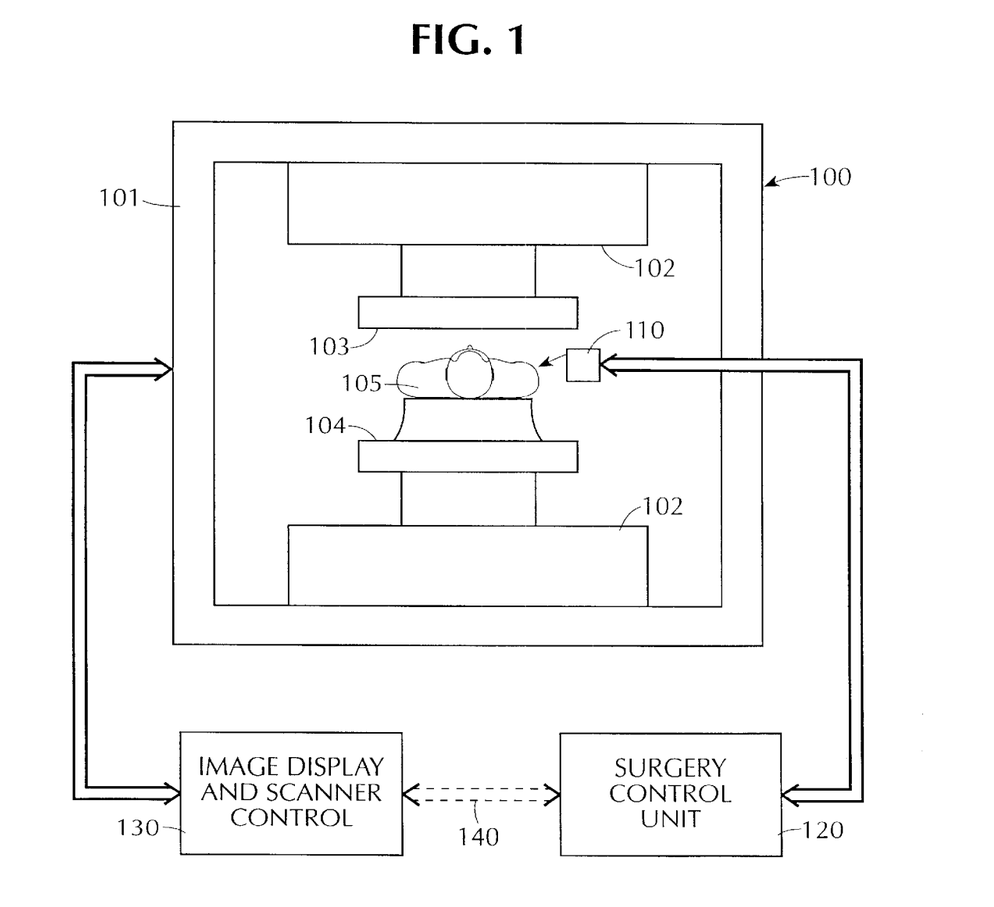
FIG. 1 illustrates an apparatus for carrying out MRI-guided invasive treatment.

FIG. 1 illustrates an apparatus which may be used to carry out MRI-guided procedures. The apparatus includes a magnet 100 which is of the type disclosed in detail in copending U.S. application Ser. No. 07/993,072, filed Dec. 18, 1992 and commonly assigned. The detailed structure of the magnet is disclosed in the copending application. The magnet 100 is generally comprised of a ferromagnetic yoke 101 which provides a magnetic flux path for a magnetic flux generated by a source of magnetic flux 102. A pair of opposed pole surfaces 103, 104 define a gap 105 between them through which- magnetic flux flows. A patient is positioned within the gap 105 for the acquisition of magnetic resonance imaging data, and to have surgical procedures carried out upon the patient under the guidance of the MRI images.

Block 110 represents means for performing surgery upon the patient. This structure can be dispensed with, and the surgery can be performed manually by a surgeon using appropriate surgical instruments.

The surgery control unit 120 exercises control over the surgical performance unit 110 and receives position and other feedback signals for carrying out the surgical procedure. The surgical performance unit 110 is defined as the remote operating device wherein remote is defined as any region outside the body including all regions adjacent to the skin. The surgical performance unit can be either a manually operated or computer operated device for advancing the surgical instrument and/or therapeutic chemical delivery instrument into the patient's interior.

The scanner control unit and image display 130 interacts with the scanner magnet 100 and ancillary scanner subsystems for carrying out MRI on the patient and displaying the images on monitors for direct viewing. The scanner control unit and image display 130 can be used for carrying out repetitive scans during the course of the surgery to allow the surgeon and assisting personnel to continuously have current images of the anatomical site undergoing surgery on display to them.

The surgery control unit 120 and scanner control unit and image display 130 are shown as separate system elements, with a communication path 140 between them. In practice, these two units may be physically integrated such that they are operated from the same console and share operator controls and display screens. The surgery control unit 120 operated in concert with the scanner control unit enables the surgeon to plan the path of the surgical device from the outside of the patient towards the target tissue. The imaging display console may possess light pen capability so the surgeon may superimpose the line of the desired surgical path on the image or he may enter the path coordinates thru a keyboard. With the light pen path superimposed on the image the surgeon may then advance the surgical device (catheter, needle etc.) towards the target tissue and monitor its course with repeated images comparing the actual course with the planned light pen course to be certain the desired path is being achieved. However, they are functionally distinct and are separately represented in the drawing figure.

Figure 2A:
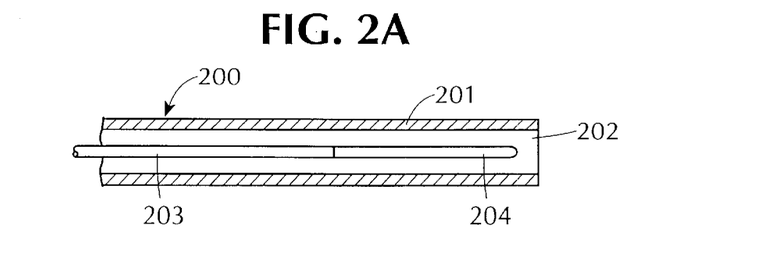
FIGS. 2A–2D illustrate the operation of a surgical instrument for use in MRI-guided surgery.

A catheter and guide combination 200 which may be used in MRI-guided procedures is shown in FIG. 2A. The catheter and guide 200 comprise a tubular catheter body 201 having an open end 202. The open end 202 constitutes the leading end of the catheter body 201 which is inserted into the body of a patient. A guide wire 203 extends through the tubular catheter 201 along its length and is movable lengthwise through the catheter 201. The guide wire 203 terminates at a movable end portion 204 which is described below. The movable end portion 204 is the leading end of the guide wire 203 when it is advanced into the body of a patient.

The use of the catheter and guide structure is shown by the sequence of FIGS. 2A–2D. Initially the catheter 201 and guide wire 203 are straight. They are inserted into the patient's body as a pair and advanced together with the catheter open end 202 and the guide wire end portion 204 advancing together as the leading ends of the structure.

Figure 2B:
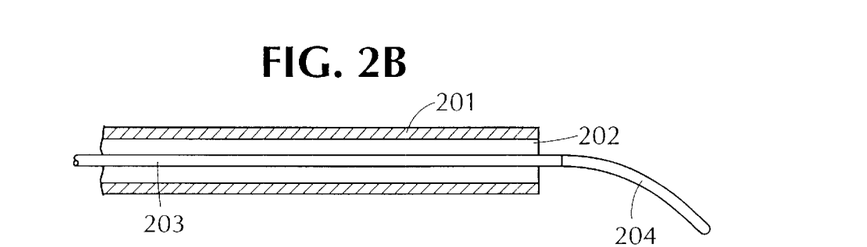

When it is desired to change the direction of advance of the catheter and guide wire the advancing of the catheter 201 is stopped while the guide wire 203 is advanced so that the guide wire end 204 extends beyond the open end 202 of the catheter 201. The end 204 of the guide wire 203 is caused to deflect toward the intended new direction of advance. This condition is shown in FIG. 2B.

Figure 2C:
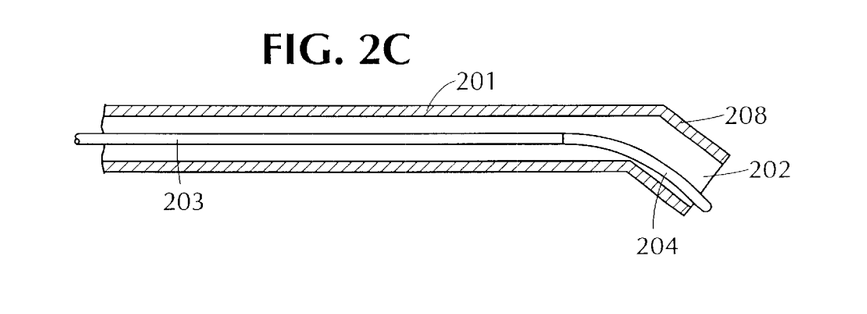

Advancement of the catheter 201 is then resumed with the open end 202 of the catheter following along the curved end portion 204 of the guide wire 203. The deflected end portion 204 causes the advancing catheter 201 to change direction as it advances with a result that a bent portion 208 is induced in the normally straight catheter 201. This condition is shown in FIG. 2C.

Figure 2D:
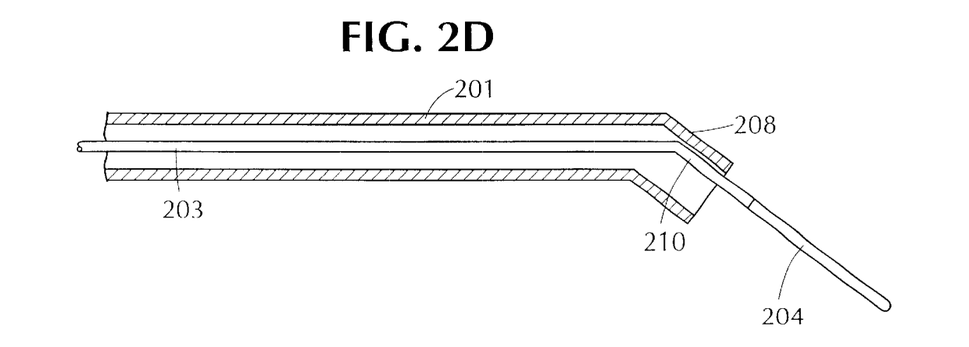

Next, the guide wire 203 is advanced in the new direction. The catheter 201 is surrounded by body tissue so that the bend 208 will not relax and straighten, even after the end portion 204 of the guide wire is advanced out through the open end 202 of the catheter 201. Consequently, as the guide wire 203 is advanced into the patient's body it will change direction at a bend 210 which is a result of the guide wire advancing against the bent portion 208 of the catheter 201. This is shown in FIG. 2D.

If the tissue surrounding the catheter is sufficiently firm, the catheter can be advanced along with the guide wire without losing the change of direction achieved by the bent portion 208 of the catheter 201. Both the catheter 201 and the guide wire 203 should be resilient so that they can be bent, and so they will also return to their relaxed shape after any bending pressure has been removed. They must likewise be sufficiently stiff to allow them to be advanced axially by pushing on them at a location remote from the advancing end. Finally, the guide wire 203 should be nonferrous to avoid image artifacts caused by magnetic field homogeneity.

Figure 3:
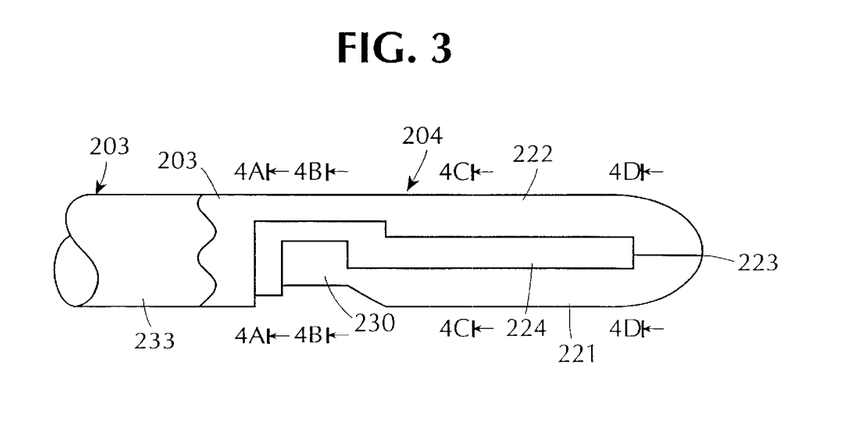
FIG. 3 illustrates details of the movable end of the surgical instrument shown in FIG. 2.

Details of the movable end portion 204 of the guide wire 203 are shown in FIG. 3. The movable end portion 204 is shown in longitudinal section and is comprised of a bimetallic structure having a lower 221 and an upper half 222. Lower half 221 and upper half 222 are each made from a different metal having a different coefficient of thermal expansion. The halves 221, 222 meet at a permanent junction 223 at the free end of the movable end portion 204.

A thin insulative layer 224 is disposed between the metal halves 221 and 222 of the movable end 204, except at the junction 223. For purposes of illustration, the insulative layer 224 is shown thicker than it would be made in practice. The guide wire 203 is comprised of a coaxial conductor for providing a current path to the movable end 204. The center conductor 230 of the guide wire is fused to the bottom half 221 of the movable end portion. An inner insulator 231 connects with the insulative layer 224 and also serves to insulate the center conductor 230 of the guide wire from the outer conductor 232. The upper half 222 of the movable end is fused to the outer conductor 232 of the guide wire, and the guide wire is covered by an outer insulative layer 233.

The structure of the movable end portion 204 of the guide wire 203 results in a series circuit for flowing current through the bimetal structure of the movable end portion 204. In particular, current flows through the center conductor 230 of the guide wire into the lower half 221 of the movable end portion and through the junction 223. The current continues through the upper half 222 of the movable end portion and back through the outer conductor 232 of the guide wire. The insulative layer 224 insures that current flows through the entire length of the bimetallic structure of the movable end portion for heating the two metal halves 221, 222 and maximizing the deflection which will occur because of their different respective thermal coefficients of expansion.

Figure 4A:
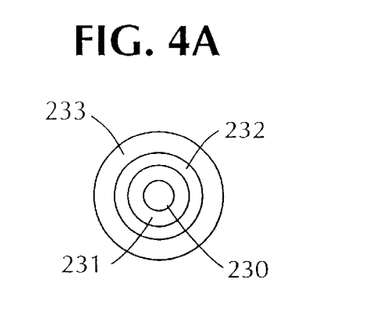
FIGS. 4A–4D are cross sections of the movable end of the instrument shown in FIG. 3.
Figure 4B:
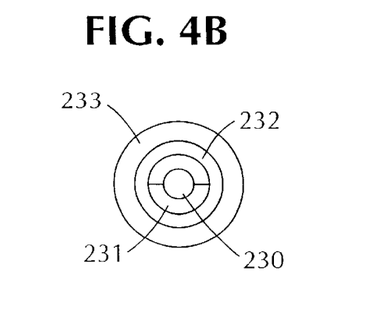
Figure 4C:
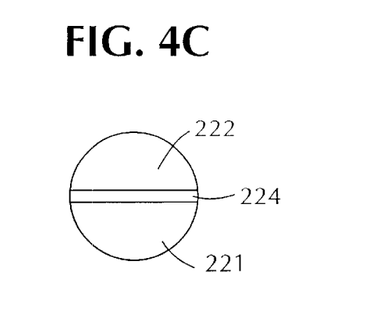
Figure 4D:
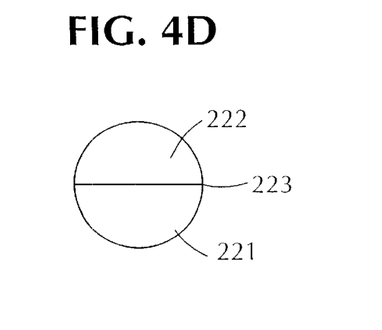

The cross-sectional structure of the movable end portion along the successive section lines in FIG. 3 is illustrated in FIGS. 4A–4D. FIG. 4A shows the concentric structure of the guide wire comprising the central conductor 230 and the outer coaxial conductor 232 with the intermediate insulating layer 231 between them. FIG. 4B shows the cross-sectional structure at the junction between the movable end 204 and the guide wire 203. FIG. 4C is a cross section through the movable end portion 204 and shows the position of the insulative layer 224 between the metallic halves 221 and 222. Finally, FIG. 4D is a cross section through the junction 223 of the two metal halves 221 and 222.

A method of fabricating the movable end portion 204 is shown in FIGS. 5A–5E. The starting components for the fabrication of the movable end portion include an upper blank 301 and a lower blank 302 shown in FIGS. 5A and 5B, respectively. The upper blank 301 has a T-shaped end 303 and is shown edgewise in the figure. The lower side of the upper blank 301 has an insulative layer 304 disposed on it. The upper blank 301 will become the upper half 222 of the movable end portion, and the insulative layer 304 will become the insulative layer 224 which is between the two halves of the movable end portion 204. The insulative layer 304 is advantageously formed by a conventional anodizing process so that it will be continuous but only a few molecules thick, and tightly adherent to the upper blank 301. Alternatively, the insulative layer 304 can be a resilient adhesive. The layer 304 is not coextensive with the length of the top blank. End portions 305 and 306 of the under side of the upper blank 301 are both free of the insulative layer 304. Region 304 is the site where the bond 223 will be formed, and region 306 is the site where the junction between the movable end portion 204 and the guide wire 203 will be formed.

Figure 5A:
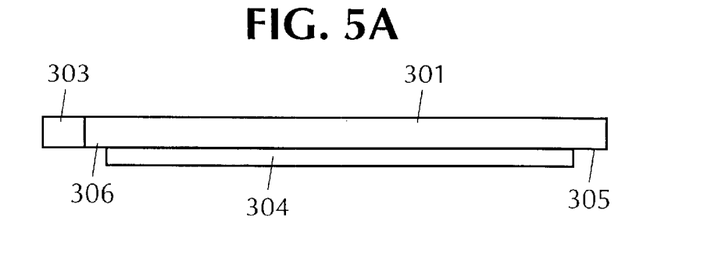
FIGS. 5A–5E illustrate the steps in fabricating the movable end of the instrument shown in FIG. 3.
Figure 5B:
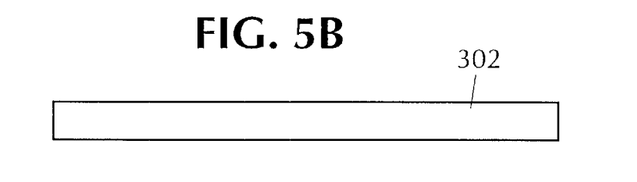

The lower blank 302 shown in FIG. 5B is somewhat shorter than the upper blank. The lower blank 302 is made of a metal different than that of the upper blank 301, and the metal comprising the lower blank 302 has a different coefficient of thermal expansion than the upper blank 301.

Figure 5C:
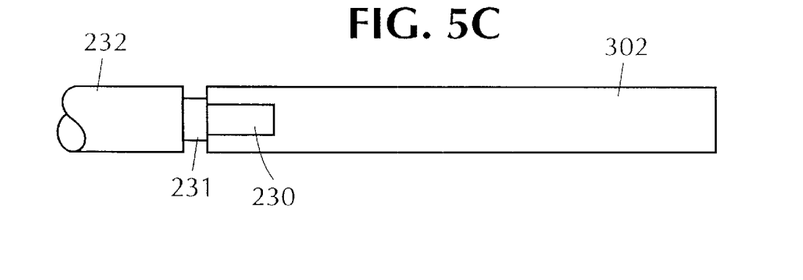
Figure 5D:
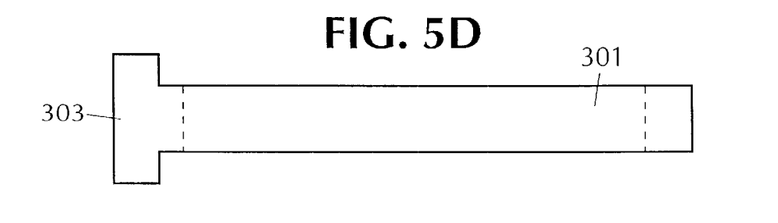

FIG. 5C is a plan view showing the lower blank 302 and the guide wire 303 positioned prior to the formation of the movable end portion 304. The center conductor 230 of the guide wire is exposed and partially overlying the end of the lower blank 302. Part of the inner insulator 231 is also exposed, and the outer conductor 232 of the guide wire 203 is exposed. The upper blank 301, shown in plan in FIG. 5D is next placed above the lower blank 302 with the T-shaped end 303 overlying the outer conductor 232 of the guide wire. This arrangement of parts is shown in FIG. 5E.

Figure 5E:
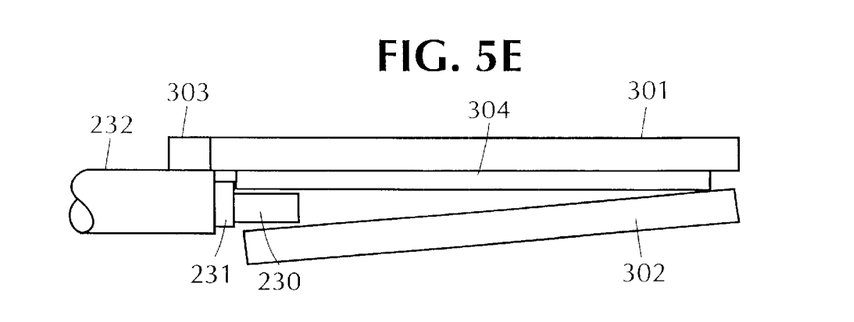

Next, the combination of elements shown in FIG. 5E is compressed and a percussive weld or bond is formed at the ends of the upper and lower blanks 301, 302 which are distant from the guide wire 203. This creates the junction 223. The upper and lower blanks 301, 302 are squeezed adjacent to each other and a percussive bond or weld is formed between the lower blank 302 and the center conductor 230 of the guide wire. Finally, the T-shaped end 303 of the upper blank is bent or swaged downward and bonded to the underlying part of the outer conductor 232 of the guide wire. The resulting structure is the movable end portion 204, and its final shaping is completed by etching and polishing finishing steps.

Figure 6:
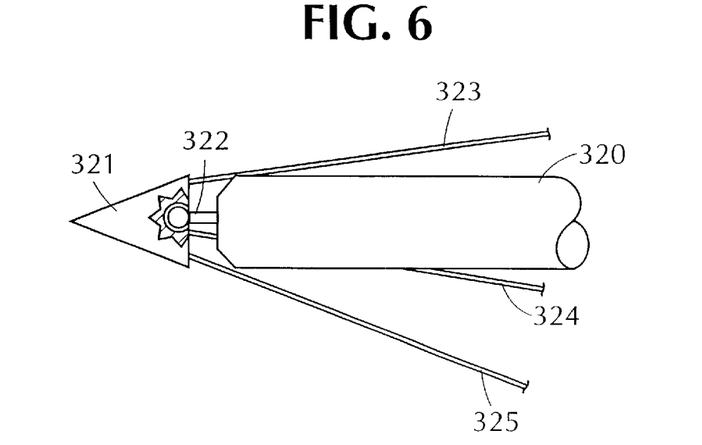
FIG. 6 illustrates another embodiment of a movable end of the instrument according to the invention.

Another embodiment of the guided instrument according to the invention is shown in FIG. 6. The instrument is comprised of a guide wire 320 having a conical head 321 mounted on one end of the guide wire. A pivot 322 mounts the head 321 for pivotal movement relative to the longitudinal axis of the guide wire 320. A plurality of control wires 323, 324 and 325 are disposed around the periphery of the head 321. Applying tension to one or more of the guide wires 323–325 is effective to pivot the head 321 on the pivot 322. Selective application of tension to different control wires allows the head 321 to be oriented in a controllable fashion. The illustrative embodiment has three control wires 323–325, but the number of control wires could be increased. The illustrative embodiment can be used with a catheter as in the previously described embodiment, or the catheter can be dispensed with. Surrounding tissue will be effective to hold the control wires 323–325 next to the guide wire 320 as the instrument advances through the tissue of a patient.

Figure 7A:
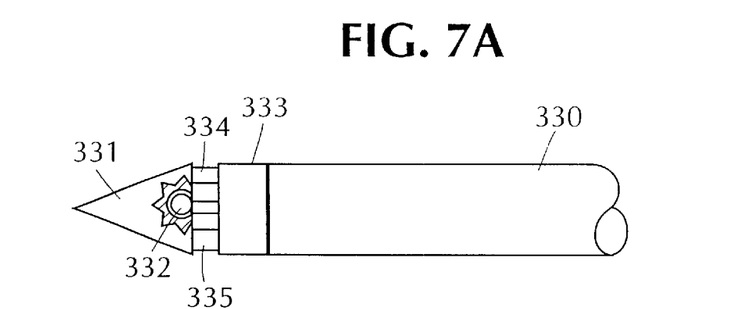
FIGS. 7A and 7B illustrate a third embodiment of a movable end of the instrument.
Figure 7B:
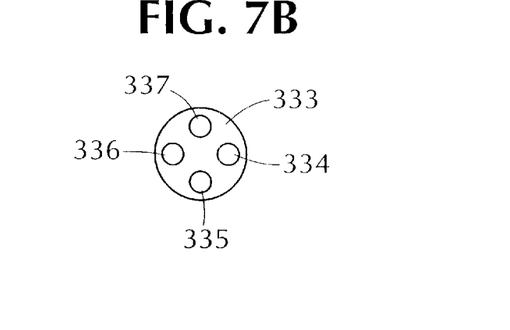

Another embodiment of the instrument is shown in FIGS. 7A and 7B. The guide wire 330 has at one end thereof a head 331 mounted by a pivot 332 on a base 333. The base 333 is fixed to the guide wire 330. A plurality of piezoelectric actuators 334, 335, 336 and 337 are disposed around the circumference of the base 333 and between the base 333 and the head 331. The layout of the piezoelectric actuators is shown in FIG. 7B.

By applying voltages to different actuators the orientation of the head 331 is varied in a pivotal motion relative to the longitudinal axis of the guide wire 330. Conductive paths extending through the guide wire 330 can provide individual voltages to the respective piezoelectric actuators to allow them to be energized independently. This embodiment of the invention is particularly advantageous because the actuating signal, an electrical voltage, can be set to a very high degree of precision and the resulting displacement of the head 331 relative to the guide wire 330 can be determined very precisely.

The instrument preferably includes a material which will give a strong MRI signal so that the instrument will appear prominently in magnetic resonance images. The instrument could comprise a tip which is paramagnetic, or alternatively the instrument tip could be opaque to MRI. The position of the instrument in a magnetic resonance image of the instrument and surrounding anatomy will appear correct relative to the surrounding anatomy. The instrument within a small region of interest or field of view can advantageously be imaged more frequently than the entire anatomy of interest, and the instrument image can be updated more frequently, to allow the instrument motion to be tracked by MRI.

The display for displaying a magnetic resonance image of the anatomy to be treated can include means for receiving a representation of the path to be followed by the instrument. The means for receiving a path representation can include a cathode ray tube for displaying the magnetic resonance image together with a light pen system which will allow the intended instrument path to be drawn on the displayed image. The advance of the instrument during the course of treatment is displayed to allow comparison between the planned and actual instrument path, and correction or adjustment of the instrument path as needed.

These catheters and guide wires can be used for carrying out various methods according to the present invention as described below. The catheter and guide wire combination are advanced through a patient to a treatment site in the manner previously established. The guide wire is then withdrawn leaving the catheter in place, and any of a variety of methods using the catheter can be commenced. Other instruments may be used as well.

The catheters and guide wires can be used for the direct delivery of a therapeutic agent, such as a therapeutic chemical or other therapeutic treatment, to the treatment site. The treatment site can be a tumor, or a tissue containing a tumor, as well as a site where a surgical treatment is to be carried out.

A therapeutic treatment may be conducted and the tissue of interest monitored by MRI to evaluate the efficacy of the therapeutic treatment. The treatment can include the systemic administration of a therapeutic chemical or other such agent. The treatment can also include the direct delivery of a therapeutic chemical or other such agent to tissue of interest. The tissue of interest is preferably monitored by repetitive MRI, particularly 3D MRI. A parameter of the therapeutic treatment, such as the amount of a therapeutic chemical delivered or the duration of a treatment, may be varied based on the results of the magnetic resonance imaging to increase the efficacy of the treatment. Changes in the image characteristics, such as the image contrast, image intensity and morphology of the tissue in the images, are indicative of the efficacy of the treatment.

The therapeutic chemical may be delivered to a tissue containing a tumor. In particular, antioxidants are introduced into the tissue, followed by monitoring MRI is used to evaluate the efficacy of the antioxidant. This method may be carried out with the further step of introducing the antioxidant directly into the tumor and simultaneously delivering a therapeutic chemical for treatment of the tumor directly into the tumor. Suitable antioxidants include a tocopherol (Vitamin E), butylated hydroxy toluene, and carotene. Preferably, the MRI is continuous, repetitive 3D MRI.

The tumor may be hepatic, pancreatic, breast, colon, lung, brain, bone, prostate, ovarian, uterine, kidney, stomach, head, neck, testicular and neurological tissue tumors, and tumors in other tissue and organs.

Where the tumor is within an organ, the therapeutic chemical or treatment can be administered to healthy regions of the organ to promote the growth of organ tissue and the repair of the tumor affected region.

The therapeutic chemical can be delivered in an unactivated state, or as an active therapeutic chemical. Activation of the therapeutic chemical can be carried out in vivo by an appropriate means. For example, the therapeutic chemical may comprise a porphyrin, such as protoporphyrin, which can be activated in vivo by light. The therapeutic chemical is first introduced, for example, into a tumor, through the catheter, and then an optical fiber is extended through the catheter into the tumor for directing light to the protoporphyrin. High intensity laser light is delivered through the optical fiber to activate the protoporphyrin within the tumor.

Another method according to the invention is a method for identifying a treatment regimen. This is carried out by administering a therapeutic chemical directly to tissue, such as to a tumor within a patient, and monitoring the tissue by MRI to determine the efficacy of the therapeutic chemical. A parameter of the treatment is adjusted and the effect of the adjustment is also monitored by MRI. The more efficacious treatment can thereby be identified.

The method just described can be augmented by administering a second therapeutic treatment (and subsequent therapeutic treatments) directly to the tissue within the patient after the efficacy of the first administered therapeutic treatment has been determined. The tissue is continuously monitored by repetitive MRI after administration of the second (and subsequent) therapeutic treatment to determine the efficacy of the latter administered therapeutic treatment. The amount of the second therapeutic treatment (or subsequent therapeutic treatments) may also be likewise adjusted in order to improve the treatment.

A variation of the methods just described is carried out by administering a plurality of therapeutic chemicals directly to separate regions of the same tumor within a patient. The tumor is continuously monitored by repetitive magnetic resonance imaging after the administration of the therapeutic chemicals to determine the effectiveness of the treatment. Thereafter, the administered amounts of selected therapeutic chemicals are adjusted to improve the treatment. One or more of the administered therapeutic chemicals are then selected for ongoing treatment of the tumor.

In another embodiment, oxygen is delivered as a therapeutic chemical. The delivery of oxygen is also used for determining the relative degree of tissue oxygenation. The tissue is imaged and then oxygen is delivered to the tissue by direct perfusion with gaseous oxygen or by administering the oxygen in combination with an oxygen carrier molecule such as hemoglobin or heme. Gaseous oxygen may be inhaled, as well. After the administration of oxygen the tissue is imaged again and the image characteristics, such as the image contrast, image intensity and the morphology of the tissue in the images, are compared. A change in image characteristics is indicative of the effect of the oxygen on the tissue. For example, the change in image characteristics can yield a relative measure of the initial degree of oxygenation of the tissue. The change in image characteristics can also be correlated with the amount of oxygen delivered to study the rate and amount of oxygen uptake of the tissue.

The oxygen delivered is predominantly oxygen-16. Preferably, only trace amounts of oxygen-17 are present. Oxygen in its naturally occurring isotopic proportions (oxygen-16, 99.76%; oxygen-18, 0.20%; oxygen-17, 0.04%) is preferred. Conventional hydrogen imaging is also preferably used. More than trace amounts of oxygen-17 could mask the effects of oxygen-16 on the tissue as measured by hydrogen imaging.

While oxygen-16 mdoes not have paramagnetic characteristics, the metabolism of oxygen-16 has effects on tissue which are discernable by MRI. For example, the effects of ischemia, such as cerebral ischemia caused by a stroke, and increased blood oxygenation in stimulated portions of the brain, have been detected by MRI. See, for example, R. Turner et al., "Functional Mapping of the Human Visual Cortex at 4 and 1.5 Tesla Using Deoxygenation Contrast EPI", MRM 29:277–279 (1993); J. H. Duijn et al., "Human Brain Infarction: Proton MR Spectroscopy", Radiology 1992; 183:711–718; D. Sappey-Marinier et al., "Decreased Phosphorus Metabolite Concentrations and Alkalosis in Chronic Cerebral Infarction", Radiology 1992; 182:29–34; P. A. Bandettini, "Time Course EPI of Human Brain Function during Task Activation", Magnetic Resonance in Medicine, 25, 390–397 (1992); K. Kwong et al., "Dynamic magnetic resonance imaging of human brain activity during primary sensory stimulation", Proc. Nat'l. Acad. Sci. USA, pp. 5675–5679, June 1992 Neurobiology; *Clinical Magnetic Resonance Imaging*, Vol. 1, edited by R. Edelman et al., "Stroke and Cerebral Ischemia, by T. M. Simonson et al., pp. 767–786, 2d ed. (1991); and L. L. Baker et al., "Recent Advances in MR Imaging/Spectroscopy of Cerebral Ischemia", AJR 156:1133–1143, June 1991.

Image contrast, and other image characteristics, also provide a measure for determining the uptake of administered therapeutic chemicals, and the uniformity of distribution of a chemical within an organ or a particular target tissue. The ability to monitor the uptake of an administered therapeutic chemical permits the development of treatment regimens. Moreover, image contrast permits determination of a desired degree of tissue perfusion and allows correct dosage of a therapeutic chemical to be selected.

The ability to monitor the uptake of a systemically administered therapeutic chemical or agent can assist in the development of pharmaceuticals, as well. In accordance with another embodiment of the invention, a pharmaceutical may be developed for an organism by delivering a drug candidate to the organism and monitoring the amount of the drug candidate absorbed by a particular tissue of interest by MRI. The amount of the drug candidate absorbed by the tissue may be determined by monitoring image characteristics, such as the image contrast, the image intensity and tissue morphology in the images, before delivery of the drug candidate and during absorption of the drug candidate by the tissue. The selectivity of the uptake by the tissue of interest may also be monitored by MRI by comparing the image characteristics of the tissue of interest and other tissue, for example. The efficacy of the drug candidate or a pharmaceutical may also be determined based on the MRI. The amount of the systemically delivered drug candidate or pharmaceutical which results in the maximum efficacy for the tissue of interest may thereby be determined.

The amount of the systemically delivered drug candidate or pharmaceutical which is actually absorbed by the tissue of interest may also be determined by MRI. The uniformity of the distribution of the drug candidate or pharmaceutical within the tissue may be determined by MRI by observing the contrast or other image characteristics across the image of the tissue, as well. The amount of the pharmaceutical absorbed by the tissue over a period of time may be monitored by monitoring the contrasts or other image characteristics of successive MR images over the period of time.

Other therapeutic chemicals which may be delivered and whose effects can be monitored in accordance with the present invention include chemicals for relevant chemotherapy and angiogenesis inhibitors. Moreover, as mentioned above, the treatment method is not limited to the delivery of a therapeutic chemical. Therapeutic agents may also be delivered and their effects monitored. For example, heat, light, radioactive seeds and radiation may also be delivered and their effects monitored by MRI. Certain of the instruments described above have means for delivering various treatment agents. Other instruments may be used to deliver such treatment agents, as well, as is known in the art. Microwave or radio frequency heating and/or ablation can also be performed. Gene therapy can be performed, as well. The parameters of the treatment, such as the intensity or duration of such treatments, can be varied and optimized by monitoring the tissue with MRI in accordance with the present invention, as well.

I claim:

1. A method of studying tissue metabolism comprising:
   acquiring a first magnetic resonance image of tissue of interest;
   delivering oxygen, predominantly in the form of oxygen-16, to the tissue of interest;
   acquiring a second magnetic resonance image of the tissue of interest after the delivery of the oxygen; and
   comparing the first and second images to determine the effect of the delivery of the oxygen on the tissue.

2. The method of claim 1, further comprising determining a relative measure of the degree of tissue oxygenation before and after delivery of the oxygen.

3. The method of claim 1, comprising delivering the oxygen through inhalation.

4. The method of claim 1, comprising delivering the oxygen directly to the tissue by perfusion.

5. The method of claim 4, comprising delivering the oxygen through a catheter.

6. The method of claim 1, comprising delivering the oxygen in combination with an oxygen carrier molecule.

7. The method claim 6, comprising delivering the oxygen in combination with an oxygen carrier molecule chosen from the group consisting of hemoglobin and heme.

8. The method of claim 6 comprising delivering the oxygen and oxygen carrier molecule through a catheter.

9. The method of claim 1, further comprising determining a relative measure of the increase in the oxygenation of the tissue of interest and correlating the increase with the amount of oxygen delivered.

10. The method of claim 1, comprising delivering oxygen-16 and trace amounts of oxygen-17.

11. The method of claim 10 comprising delivering oxygen substantially in its naturally occurring isotopic proportions.

12. A method of studying tissue metabolism comprising:
    acquiring a first magnetic resonance image of tissue of interest;
    delivering oxygen, substantially in its naturally occurring isotopic proportions, to the tissue of interest through inhalation;
    acquiring a second magnetic resonance image of the tissue of interest after the delivery of the oxygen; and
    comparing the first and second images to determine the effect of the delivery of the oxygen on the tissue.

13. A method of studying tissue metabolism comprising:
    acquiring a first magnetic resonance image of tissue of interest;
    delivering oxygen, substantially in its naturally occurring isotopic proportions, to the tissue of interest in combination with an oxygen carrier molecule;
    acquiring a second magnetic resonance image of the tissue of interest after the delivery of the oxygen; and
    comparing the first and second images to determine the effect of the delivery of the oxygen on the tissue.

14. The method claim 13 comprising delivering the oxygen and oxygen carrier molecule through a catheter.

15. The method claim 13 comprising delivering the oxygen in combination with an oxygen carrier molecule chosen from the group consisting of hemoglobin and heme.

16. A method of studying tissue metabolism comprising:
    acquiring a first magnetic resonance image of tissue of interest;
    delivering oxygen, substantially in its naturally occurring isotopic proportions, to the tissue of interest by perfusion;
    acquiring a second magnetic resonance image of the tissue of interest after the delivery of the oxygen; and
    comparing the first and second images to determine the effect of the delivery of the oxygen on the tissue.

17. The method of claim 16, comprising delivering the oxygen through a catheter.

* * * * *

UNITED STATES PATENT AND TRADEMARK OFFICE
CERTIFICATE OF CORRECTION

PATENT NO. : 6,280,383 B1  Page 1 of 1
DATED : August 28, 2001
INVENTOR(S) : Raymond V. Damadian It is certified that error appears in the above-identified patent and that said Letters Patent is hereby corrected as shown below:

<u>Title page,</u>
Item [54], change the Title to read:

-- METHOD OF STUDYING THE EFFECTS OF OXYGEN-16 DELIVERY ON TISSUE USING MAGNETIC RESONANCE IMAGING --.
Item [75], change the Inventor's Name to: -- Raymond V. Damadian --.
Item [56], "OTHER PUBLICATIONS", last entry, change "Scannig" to -- Scanning --.

<u>Column 1,</u>
Line 7, change "abandoned which" to -- now abandoned, which --

<u>Column 8,</u>
Line 15, change "ndoes" to -- does --.

<u>Column 9,</u>
Line 51, after "method" insert -- of --.

<u>Column 10,</u>
Lines 34 and 36, after "method", insert -- of --.

Signed and Sealed this

Twenty-seventh Day of August, 2002

*Attest:*

JAMES E. ROGAN
*Attesting Officer*  *Director of the United States Patent and Trademark Office*